United States Patent
Bal et al.

(10) Patent No.: US 8,697,916 B2
(45) Date of Patent: Apr. 15, 2014

(54) PROCESS FOR THE PREPARATION OF CU—CR OXIDES FOR SELECTIVE OXIDATION REACTIONS

(71) Applicant: Council of Scientific & Industrial Research, New Delhi (IN)

(72) Inventors: Rajaram Bal, Dehradun (IN); Bipul Sarkar, Dehradun (IN); Shubhra Acharyya Shankha, Dehradun (IN); Shilpi Ghosh, Dehradun (IN); Chandrashekar Pendem, Dehradun (IN); Kumar Jagdish, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 21 days.

(21) Appl. No.: 13/623,618

(22) Filed: Sep. 20, 2012

(65) Prior Publication Data

US 2013/0085305 A1 Apr. 4, 2013

(30) Foreign Application Priority Data

Sep. 22, 2011 (IN) .......................... 2766/DEL/2011

(51) Int. Cl.
  *C07C 45/36* (2006.01)
  *C07C 37/06* (2006.01)
  *B01J 23/00* (2006.01)

(52) U.S. Cl.
  USPC ........... 568/311; 568/430; 568/803; 502/305; 502/317

(58) Field of Classification Search
  USPC .................. 568/311, 430, 803; 502/305, 317
  See application file for complete search history.

(56) References Cited

PUBLICATIONS

Ralph Conner et al., "The Preparation of Cooper-Chromium Oxide Catalysts for Hydrogenation," A Communication from the Laboratory of Organic Chemistry, University of Wisconsin, vol. 54, Mar. 5, 1932, pp. 1138-1145.
T. Vales-Solis et al., "Preparation of Nanosized Perovskites and Spinels through a Silica Xerogel Template Route," Chemistry of Materials, vol. 17, Apr. 19, 2005, pp. 1919-1922.
Yohei Tanaka et al., "Influence of preparation method and additive for Cu—Mn spinel oxide catalyst on water gas shift reaction of reformed fuels," Applied Catalysis A: General 279 (2005), pp. 59-66.
Wei Li et al., "Cu—Cr—O nanocomposites: Synthesis and characterization as catalysts for solid state propellants," Solid State Sciences 9 (2007), pp. 755-755.
R. Rajeev et al., "Thermal decomposition studies. Part 19. Kinetics and mechanism of thermal decomposition of copper ammonium chromate precursor to copper chromite catalyst and correlation of surface parameters of the catalyst with propellant burning rate," Thermochimica Acta 254 (1995) pp. 235-247.
Zhigiang Ma et al., "A non-alkoxide sol-gel route to highly active and selective Cu—Cr catalysts for glycerol conversion," Journal of Material Chemistry, 2010, 20, pp. 755-760.
Vasile Georgescu et al., "Total Oxidataion of Benzene Using Cu—Cr Mixed Oxide as Catalyst," Akademiai Kiado, Budapest and Springer, Dordrecht, vol. 94, No. 2 (2008) pp. 345.350.
Galina Xanthopoulou et al., "Investigation of catalytic oxidation of carbon monoxide over a Cu—Cr-oxide catalyst made by self-propagating high-temperature synthesis," Applied Catalysis B: Environmental 19 (1998) pp. 37-44.

*Primary Examiner* — Sikarl Witherspoon
(74) *Attorney, Agent, or Firm* — Blank Rome LLP

(57) ABSTRACT

The present invention provides a process for the preparation of Cu—Cr oxides by hydrothermal synthesis method using hydrazine as a reducing agent and cetyltrimethylammonium bromide as a surfactant and these oxides are very active for selective oxidation of benzene, toluene and ethylbenzene to produce phenol, benzaldehyde and acetophenone, respectively.

12 Claims, 3 Drawing Sheets

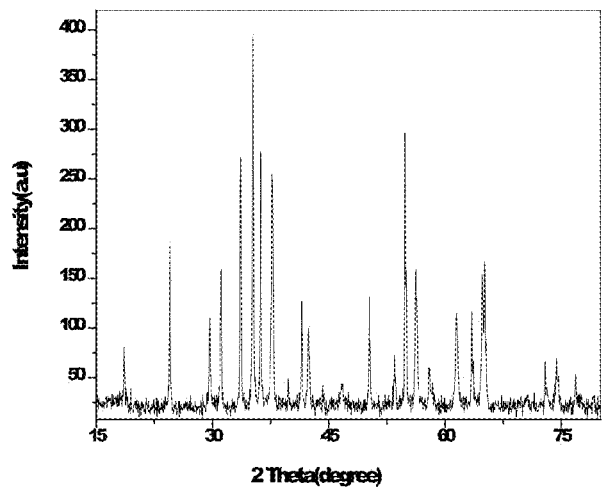
Fig 1 : XRD
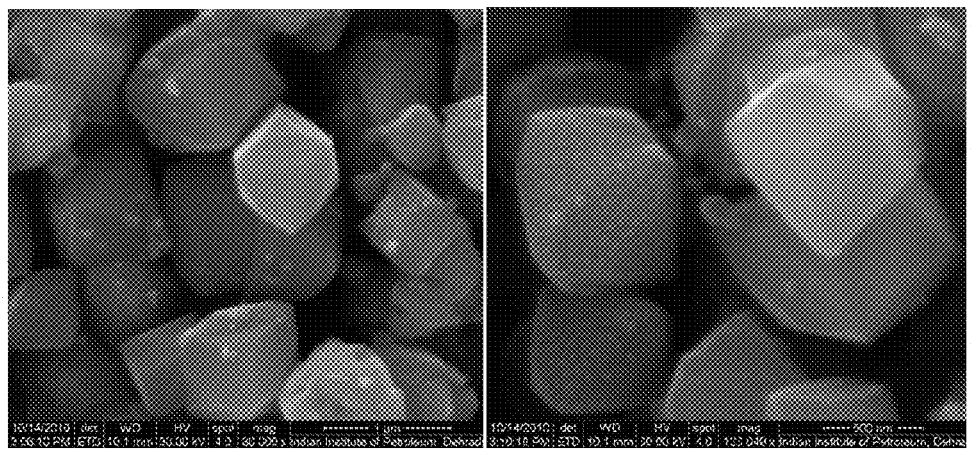
Fig 2 : SEM

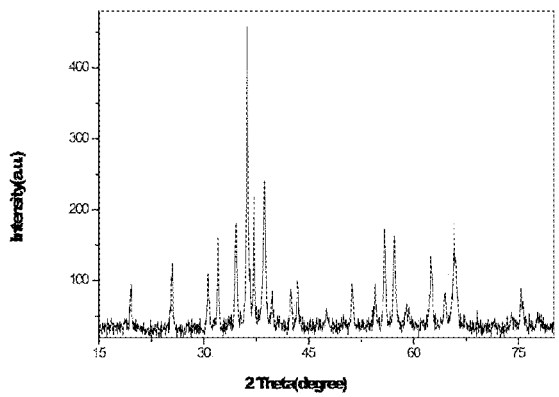
Fig 3 : XRD (X-ray Diffraction):
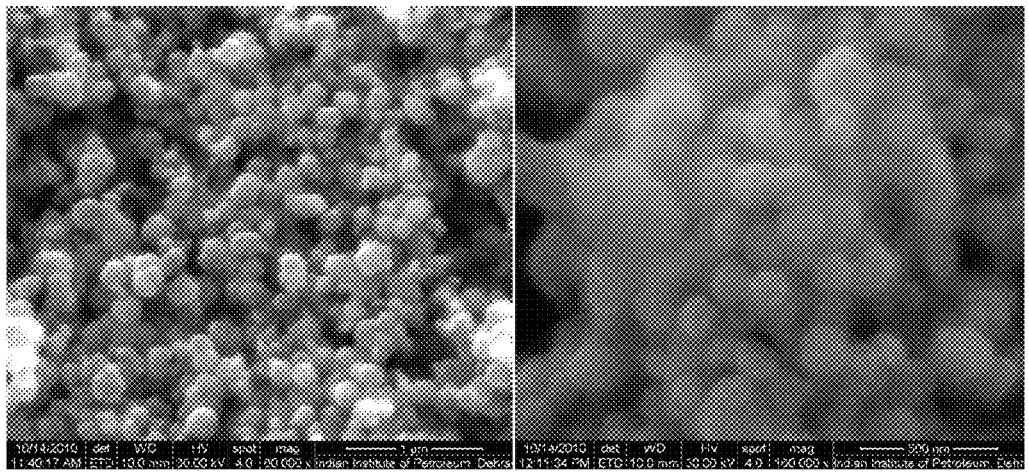
Fig 4 : SEM (Scanning Electron Microscope):

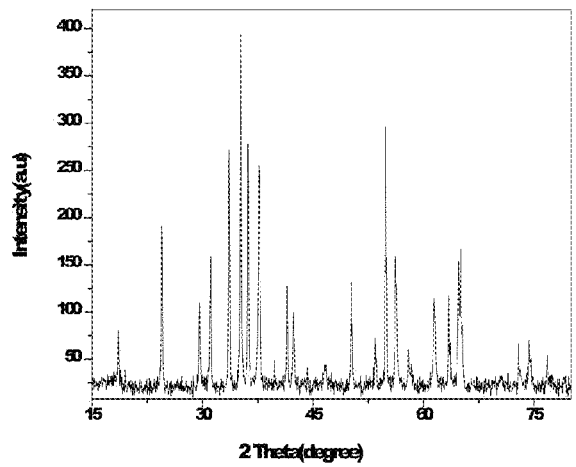
Fig 5 : XRD:
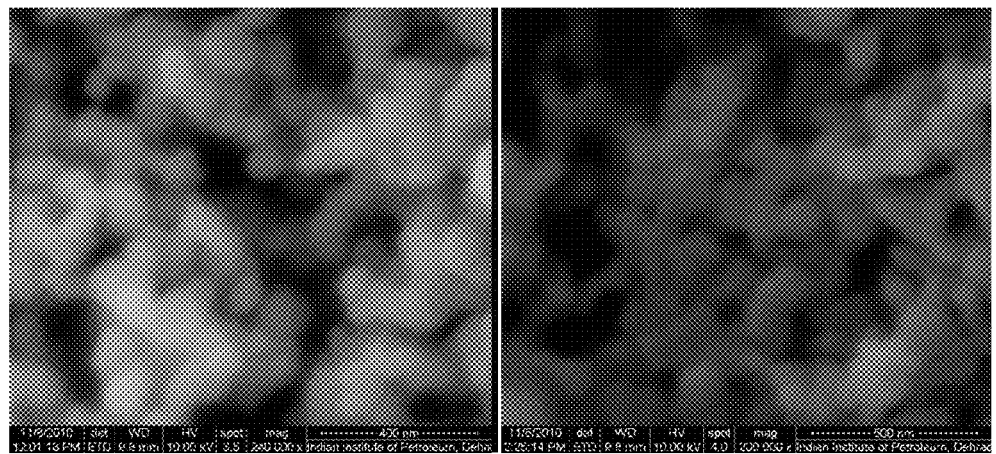
Fig 6: SEM:

PROCESS FOR THE PREPARATION OF CU—CR OXIDES FOR SELECTIVE OXIDATION REACTIONS

FIELD OF INVENTION

The present invention relates to a process for the preparation of Cu—Cr oxide as catalyst for selective oxidation reactions. More particularly, the present process relates to an improved process for the formation of Cu—Cr mixed oxide by hydrothermal synthesis method using hydrazine as a reducing agent and cetyltrimethylammonium bromide as a surfactant. The present invention also relates to single step selective oxidation of benzene, toluene and ethylbenzene using Cu—Cr oxide catalysts.

BACKGROUND OF INVENTION

Cu—Cr—O composite materials are usually prepared by a variety of synthetic methods, involving the reduction of Cu—Cr oxide prepared by Adkins' route, template method, citric acid complex method, precipitation and thermal decomposition, conventional high temperature method, coprecipitation method, gel method, hydrothermal method, microemulsion method, heterogeneous precipitation method, sonochemical method, combustion method, sol-gel method. These methods allow substantial reduction of the temperature of precessing, minimizing therefore the undesired aggregation of the particles during calcinations. Among these methods, the sol-gel process shows promising potential for the synthesis of mixed oxides, owing to its high purity, good chemical homogeneity, low calcinations temperature, etc. The major disadvantages of using the metal alkoxides based sol-gel process are its moisture sensitivity and the unavailability of suitable commercial precursors especially for mixed-metal oxides. The sol-gel synthesis of mixed metal oxides from alkoxide mixture usually suffers from the different hydrolysis susceptibilities of the individual components and the benefits of improved homogeneity can be lost during the hydrolysis of the alkoxides, which may ultimately lead to component segregation and mixed phases in the final materials. Non-alkoxide sol-gel process, involving hydrolysis and condensation of metal salts, avoids the disadvantages of alkoxide sol-gel process, however has still the disadvantage of different hydrolysis susceptibilities of the individual components.

These preparation methods are not good enough largely because many of their metal alkoxides are expensive, and still others are sensitive to moisture, heat, and light making their use and long-term storage difficult. In addition, some metal alkoxide are not commercially available or are difficult to obtain, thus precluding detailed studies on the preparation and application. The main advantage of our process that no alkoxide is used in this process and the preparation method is highly reproducible. The yield is also very high and it is as much as 95%. To the best of our knowledge there is no report for the preparation of Cu—Cr oxide using hydrazine and cetyltrimethylammonium bromide.

Reference may be made to the article J. Am. Chem. Soc. 54 (1932) 1138 by Adkins et al where they decomposed copper ammonia chromate precipitation to prepare Cu—Cr oxide. Reference may also be made to the article Chem. of Materials 17 (2005) 1919 where A. B. Futertes et al used silica xerogel as the template to synthesize the $CuCr_2O_4$ spinels. Reference may also be made to the article Appl. Catal A: 279 (2005) 59 by Tanaka et al where they used citric acid complex method to synthesize Cu—Cr oxide materials. Reference may also be made to the articles Solid State Sci. 9 (2007) 750 where Cheng et al has used the precipitation method to prepare Cu—Cr oxide materials. Reference may also be made to the articles Thermochim Acta 254 (1995) 235 where Nair et al used thermal decomposition method to stnthesize Cu—Cr oxide. Reference may also be made to the articles J. Mater. Chem. 20 (2010) 755 by Liang et al where they used non-alkoxide sol-gel route to prepare Cu—Cr oxide materials. Cu—Cr oxide have been used as catalyst for the chemical reactions of hydrogenation, dehydrogenation, alkylation, oxidation, in car exhaust purification. Although, there are only few reports for the oxidation over Cu—Cr oxide catalysts, but to the best of our knowledge there is no report where a single catalyst is used for the selective oxidation of benzene, toluene and ethylbenzene with very good selectivity.

Reference may also be made to the articles Reac. Kinec. Catal. Lett. 94 (2008) 345 by Ionescu et al where they used Cu—Cr oxide catalyst was used for the total oxidation of benzene to get $CO_2$. Reference may also be made to the articles Appl. Catal. B-Environmental 19 (1998) 37 by Vekinis Vekinis et al where Cu—Cr oxide was used for the oxidation of carbon monoxide.

Thus, although there are some reports for the selective oxidation of benzene, toluene and ethylbenzene using different heterogeneous catalysts, but there is no reports where Cu—Cr oxide was used for these oxidation reactions. Additionally the catalyst used have a limited activity under operating condition, so improvement of the catalysts is necessary for industrial application.

OBJECTIVES OF THE INVENTION

The main object of the present invention is to provide a process for the preparation of Cu—Cr oxides as catalyst for selective oxidation reactions which obviates the drawbacks of hitherto known methods as detailed above.

Another object of the present invention is to provide a process for the preparation of Cu—Cr oxide by hydrothermal synthesis method.

Still another object of the present invention is to provide a Cu—Cr oxide catalyst for single step selective oxidation of benzene, toluene, ethylbenzene using hydrogen peroxide as an oxidant.

Yet another object of the present invention is to provide a process which gives very high conversion of benzene, toluene and ethylbenzene with high selectivity of phenol, benzaldehyde and acetophenone, respectively.

Yet another object of the present invention is to provide a process for the preparation of Cu—Cr oxide by hydrothermal method using hydrazine as a reducing agent and cetyltrimethylammonium bromide as a surfactant.

Yet another object of the present invention is to provide a process for the preparation of Cu—Cr oxide, which shows very high activity for selective oxidation of benzene, toluene and ethylbenzene in the liquid phase with hydrogen peroxide.

SUMMARY OF THE INVENTION

Accordingly, the present invention provides a process for the preparation of Cu—Cr oxide, wherein the process comprising the steps of:
  a. mixing of $Cu(NO_3)_2.3H_2O$ and $Cr(NO_3)_3.9H_2O$ solution, where the molar ratio of Cu to Cr ranges between 0.05-0.7,
  b. adding a surfactant solution drop wise into the solution as obtained in step (a) with constant stirring, where the molar ratio of Cu to surfactant ranges between 0.5 to 1.5, c. adding of a reducing agent drop wise into the solution as obtained in step (b) with constant stirring to obtain a gel where the molar ratio of Cu to reducing agent ranges between 0.5 to 1.5, d. heating the gel as obtained in step (c) at temperature ranging between 30-55° C. for a period ranging between 2-4 hrs followed by heating the gel at temperature ranging between 100-200° C. hydrothermally for a period ranging between 12-30 hours to obtain solid catalyst followed by washing the solid with excess water, e. drying the solid catalyst as obtained in step (d) at 80-110° C. for a period ranging between 6-24 h.

f. calcining the solid catalyst as obtained in step (e) at temperature ranging between 300-900° C. for a period of 5-12 to obtain Cu—Cr oxide catalyst.

In an embodiment of the invention, surfactant used in step (b) is cetyltrimethyl ammonium bromide (CTAB).

In one embodiment of the invention, reducing agent used in step (c) is hydrazine.

Another aspect of the invention relates to a process for selective oxidation of aromatic using catalyst wherein the process comprising the steps of:

i) reacting aromatic substrate with an oxidant in an solvent in presence of Cu—Cr oxide catalyst wherein weight ratio of the substrate to catalyst is in the range of 3 to 20, and molar ratio of substrate to oxidant in the range of 1:2 to 1:30 at temperature in the range of 30-120° C., ii) agitating the reaction mixture for a period of 1-30 hours, followed by cooling to room temperature to obtain the products.

In yet another embodiment, the aromatic substrate used is selected from the group consisting of benzene, toluene and ethylbenzene.

In yet another embodiment, the oxidant used is $H_2O_2$ In still another embodiment, obtained the products are selected from the group of phenol, benzaldehyde and acetophenone based on aromatic substrate.

In still another embodiment, the conversion of benzene to phenol is in the range of 8-100% In still another embodiment, the conversion of toluene to benzaldehyde is in the range of 5-95%.

In still another embodiment, the conversion of ethylbenzene to acetophenone is in the range of 20-94%.

In still another embodiment, the selectivity of the phenol, benzaldehyde, acetophenone is in the range of 50 to 100%.

In still another embodiment, yield of the phenol, benzaldehyde, acetophenone is in the range of 12-91%.

BRIEF DESCRIPTION OF DRAWING

FIG. 1 XRD of Cu—Cr oxide as prepared in example 1 (JCPDS card no: [: 5-0657] Formation of $CuCr_2O_4$ spinel)

FIG. 2 SEM of Cu—Cr oxide as prepared in example 1

FIG. 3 XRD of Cu—Cr oxide as prepared in example 2 (JCPDS card no:[5-0657]/[26-1113]: Formation of $CuCr_2O_4$ spinel in addition with the small amount of $CuCrO_2$ spinel.)

FIG. 4 SEM of Cu—Cr oxide as prepared in example 2

FIG. 5 XRD of Cu—Cr oxide as prepared in example 3 (JCPDS card no: [5-0657]/[6-0504]: Formation of $CuCr_2O_4$ spinel)

FIG. 6 SEM of Cu—Cr oxide as prepared in example 3

DETAILED DESCRIPTION OF THE INVENTION

The present invention provides a process for the preparation of Cu—Cr oxide by hydrothermal synthesis method for the selective oxidation of benzene, toluene and ethylbenzene in the liquid phase reaction using hydrogen peroxide as an oxidant involves the following steps: preparation of the gel composition using $Cu(NO_3)_2.3H_2O$, $Cr(NO_3)_3.9H_2O$, Cetyltrimethylammonium bromide (CTAB), Hyrazine, $H_2O$ where $Cu(NO_3)_2.3H_2O$ and $Cr(NO_3)_3.9H_2O$ are the precursors for Cu and Cr respectively.

The molar ratio of Cu to Cr was varied in the range between 0.1 to 0.5 (Cu:Cr=0.1 to 0.5)

The molar ratio of Cu to CTAB varied in the range of 0.75-1.3.

The molar ratio of Cu to hydrazine varied in the range of 0.75-1.3.

The mixing gel was transferred in a Teflon-lined Stainless steel autoclave and kept in an oven with temperature range of 150-180° C. for 20-24 hours.

The product was filterer with excess water and dried in an oven with temperature range of 100-120° C. The dried product was calcined in a furnace in the temperature range of 300-750° C.

General Procedure for Selective Oxidation

Liquid phase selective oxidation reaction was carried out in a two neck Round Bottom flask containing catalyst, acetonitrile and substrate (reactant) to which oxidant was added. Then the reaction mixture was stirred at 70° C. for several hours. After completion of the reaction, the reaction mixture was cooled in a cold water at a temperature 10° C. and analyzed by GC fitted with a capillary column and FID detector.

The following examples are given by way of illustration of the working of the invention in actual practice and should not be construed to limit the scope of the present invention in any way.

Example 1

40 g $Cr(NO_3)_3.9H_2O$ was dissolved in 40 g water and 2.95 g $Cu(NO_3)_2.3H_2O$ was added to it. Into this solution, 3.9 g cetyltrimethylammonium bromide dissolved with 5 g $H_2O$ was added dropwise to get a homogeneous mixture. Then 0.5 g hydrazine dissolved with 2 g water was added dropwise to this mixture. The gel formed was stirred for 3 h at 35° C. and finally the mixture was hydrothermally treated at 180° C. for 24 hours in a Teflon lined stainless steel autoclave under a autogeneous pressure. The product was washed with excess distilled water and ethanol and dried at 110° C. for 24 hours and calcined in the temperature at 750° C. for 6 hrs in air.

Example 2

27 g $Cr(NO_3)_3.9H_2O$ was dissolved in 350 g water and 19.1 g $Cu(NO_3)_2.3H_2O$ was added to it. Into this solution, 21.5 g cetyltrimethylammonium bromide dissolved with 50 g $H_2O$ was added dropwise to get a homogeneous mixture. Then 4.9 g hydrazine dissolved with 10 g water was added dropwise to this mixture. The gel formed was stirred for 3 h at 50° C. and finally the mixture was hydrothermally treated at 180° C. for 24 hours in a Teflon lined stainless steel autoclave under a autogeneous pressure. The product was washed with excess distilled water and ethanol and dried at ambient temperature for 24 hours and calcined in the temperature between 650° C. for 6 hours in air.

Example 3

60 g $Cr(NO_3)_3.9H_2O$ was dissolved in 750 g water and 39 g $Cu(NO_3)_2.3H_2O$ was added to it. Into this solution, 42 g cetyltrimethylammonium bromide dissolved with 90 g $H_2O$ was added dropwise to get a homogeneous mixture. Then 9.2 g hydrazine dissolved with 18 g water was added dropwise to this mixture. The gel formed was stirred for 3 h at 35° C. and finally the mixture was hydrothermally treated at 150° C. for 24 hours in a Teflon lined stainless steel autoclave under a autogeneous pressure. The product was washed with excess distilled water and ethanol and dried at ambient temperature for 24 hours and calcined in the temperature between 550° C. for 7 hrs in air.

Example 4

This example describes the hydroxylation of benzene by hydrogen peroxide using the above catalyst (Example 1)

Process Conditions:

Catalyst: 0.1 g

Cu:Cr molar ratio in the catalyst=1:4.8

Benzene: 1 g

Acetonitrile: 10 ml $H_2O_2$: 5 ml

Temperature: 70° C.

Time: 24 h

Product analysis:

Benzene conversion: 98.4%

Yield of Phenol: 90.5%

Selectivity of Phenol: 92%

TABLE 1

Effect of metal loading on benzene conversion phenol yield and selectivity

| Metal (Cu) loading (wt %) | Benzene Conversion (%) | Phenol Yield | Selectivity |
|---|---|---|---|
| 5 | 20 | 20 | 100 |
| 10 | 98 | 86.2 | 88 |
| 30 | 98 | 90.1 | 92 |
| 50 | 97 | 79.5 | 82 |

TABLE 2

Effect of temperature on benzene conversion, phenol yield and selectivity

| Temperature (° C.) | Benzene Conversion (%) | Phenol Yield | Selectivity |
|---|---|---|---|
| 35 | 8 | 8 | 100 |
| 70 | 98 | 90.1 | 92 |
| 100 | 99 | 69.3 | 70 |

TABLE 3

Effect of solvent on benzene conversion, phenol yield and selectivity

| Solvent | Benzene Conversion (%) | Phenol Yield | Selectivity |
|---|---|---|---|
| acetonitrile | 98 | 90.1 | 92 |
| dioxan | 70 | 56 | 80 |
| isooctane | 40 | 28 | 70 |
| dimethylsulfoxide | 60 | 36 | 60 |

TABLE 4

Effect of benzene:H2O2 mole ratio on benzene conversion, phenol yield and selectivity

| Benzene:H2O2 mole ratio | Benzene Conversion (%) | Phenol Yield | Selectivity |
|---|---|---|---|
| 1:2.5 | 30 | 30 | 100 |
| 1:5 | 98 | 90.1 | 92 |
| 1:10 | 100 | 65 | 65 |
| 1:20 | 100 | 60 | 60 |

TABLE 5

Effect of time on stream on benzene conversion, phenol yield and selectivity

| Time (hrs) | Benzene Conversion (%) | Phenol Yield | Selectivity |
|---|---|---|---|
| 1 | 12 | 12 | 100 |
| 3 | 30 | 30 | 100 |
| 6 | 45 | 45 | 100 |
| 12 | 75 | 71.2 | 95 |
| 24 | 98 | 90.1 | 92 |

Example 5

This example describes the hydroxylation of toluene by hydrogen peroxide using the above catalyst (Example 2)

Process Conditions:

Catalyst: 0.1 g

Cu:Cr molar ratio in the catalyst=1:4.8

Toluene: 1 g

Isooctane: 10 ml $H_2O_2$: 5 ml

Temperature: 70° C.

Time: 24 h

Product analysis:

Toluene conversion: 88.1%

Yield of Benzaldehyde: 88.1

Selectivity of Benzaldehyde: 100%

TABLE 6

Effect of Toluene:H2O2 mole ratio on Toluene conversion, Benzaldehyde yield and selectivity

| Toluene:H2O2 Mole ratio | Toluene Conversion (%) | Benzaldehyde Yield | Selectivity |
|---|---|---|---|
| 1:2.5 | 68 | 50.32 | 74 |
| 1:5 | 88 | 88 | 100 |
| 1:10 | 92 | 64.4 | 70 |
| 1:20 | 94 | 61.1 | 65 |

TABLE 7

Effect of solvent mole ratio on Toluene conversion, Benzaldehyde yield and selectivity

| solvent | Toluene Conversion (%) | Benzaldehyde Yield | Selectivity |
|---|---|---|---|
| acetonitrile | 70 | 45.5 | 65 |
| isooctane | 88 | 88 | 100 |

TABLE 7-continued

Effect of solvent mole ratio on Toluene conversion, Benzaldehyde yield and selectivity

| solvent | Toluene Conversion (%) | Benzaldehyde Yield | Selectivity |
|---|---|---|---|
| dioxan | 30 | 21 | 70 |
| Dimethyl sulfoxide | 45 | 24.7 | 55 |

TABLE 8

Effect of time on stream on Toluene conversion, Benzaldehyde yield and selectivity

| Time (hrs) | Toluene Conversion (%) | Benzaldehyde Yield | Selectivity |
|---|---|---|---|
| 1 | 5 | 48.5 | 97 |
| 3 | 17 | 12.75 | 75 |
| 6 | 25 | 22.75 | 91 |
| 12 | 70 | 70 | 100 |
| 24 | 88 | 88 | 100 |

TABLE 9

Effect of weight of catalyst on Toluene conversion, Benzaldehyde yield and selectivity

| Catalyst weight (gm) | Toluene Conversion (%) | Benzaldehyde Yield | Selectivity |
|---|---|---|---|
| 0.01 | 2 | .18 | 9 |
| 0.05 | 88 | 88 | 100 |
| 0.1 | 90 | 63 | 70 |
| 0.5 | 95 | 57 | 60 |
| 1 | 95 | 38 | 40 |

Example 6

This example describes the hydroxylation of ethylbenzene by hydrogen peroxide using the above catalyst (Example 3)
Process Conditions:
Catalyst: 0.1 g
Cu:Cr molar ratio in the catalyst=1:4.8
Ethylbenzene: 1 g
Acetonitrile: 10 ml
$H_2O_2$: 5 ml
Temperature: 70° C.
Time: 6 h
Product analysis:
Ethylbenzene conversion: 73.1%
Yield of Acetophenone: 66.8%
Selectivity of Acetophenone: 91.4%

TABLE 10

Effect of Ethylbenzene:H2O2 mole ratio on Ethylbenzene conversion, Acetophenone yield and selectivity

| Ethylbenzene:H2O2 Mole ratio | Ethylbenzene Conversion (%) | Acetophenone Yield | Selectivity |
|---|---|---|---|
| 1:2.5 | 43 | 38.7 | 90 |
| 1:5 | 75 | 69 | 92 |
| 1:10 | 80 | 56 | 70 |
| 1:20 | 94 | 61.1 | 65 |

TABLE 11

Effect of solvent on Ethylbenzene conversion, Acetophenone yield and selectivity

| Solvent | Ethylbenzene Conversion (%) | Acetophenone Yield | Selectivity |
|---|---|---|---|
| acetonitrile | 75 | 69 | 92 |
| isooctane | 30 | 18 | 60 |
| dioxan | 23 | 16.1 | 70 |
| dimethylsulfoxide | 40 | 20 | 50 |

TABLE 12

Effect of time on stream on Ethylbenzene conversion, Acetophenone yield and selectivity

| Time (hrs.) | Ethylbenzene Conversion (%) | Acetophenone Yield | Selectivity |
|---|---|---|---|
| 1 | 20 | 18.8 | 94 |
| 3 | 45 | 41.4 | 92 |
| 6 | 75 | 68.25 | 91 |
| 12 | 85 | 72.2 | 85 |
| 24 | 90 | 72 | 80 |

Example 7

The example demonstrates the recyclability of the catalyst in the hydroxylation of benzene to phenol. The phenol yield patterns of fresh and recycled catalysts are given in Table 1. After the completion of the reaction, the reaction mixture was extracted with ether. The aqueous layer was separated and dried in oven at 120° C. and solid residue was used. The results of using the recycled catalyst are shown in Table 1.
Process Conditions:
Catalyst: 0.1 g
Cu:Cr molar ratio in the catalyst=1:4.8
Benzene: 1 g
Acetonitrile: 10 ml
$H_2O_2$: 5 ml
Temperature: 70° C.
Time: 24 h

TABLE 13

Effect of catalyst recycling on benzene conversion and yield and selectivity of phenol

| Catalyst | Benzene Conversion (%) | Phenol Yield | Selectivity |
|---|---|---|---|
| Fresh | 98.4 | 90.5 | 92 |
| One time recycled | 96.2 | 89.5 | 93 |
| Two time recycled | 97.0 | 88.3 | 91 |
| Three time recycled | 95.1 | 87.5 | 92 |

The main advantages of the present invention are:
1. The process of the present invention prepares a catalyst Cu—Cr oxide by hydrothermal synthesis method for the selective oxidation reaction.
2. The process of the present invention converts benzene to phenol in a single step with a single catalyst.
3. The process of the present invention converts toluene to benzaldehyde in a single step with a single catalyst.
4. The process of the present invention converts ethylbenzene to acetophenone in a single step with a single catalyst.

5. The process provides not only good conversion but also good selectivity.
6. The catalyst is used in very low amounts.

We claim:

1. A process for the preparation of Cu—Cr oxide as catalyst, the process comprising the steps of:
   a. mixing of $Cu(NO_3)_2.3H_2O$ and $Cr(NO_3)_3.9H_2O$ to obtain a solution, wherein the molar ratio of Cu to Cr is in the range of 0.05-0.7,
   b. adding a surfactant drop wise into the solution as obtained in step (a) with constant stirring, wherein the molar ratio of Cu to surfactant in the obtained solution is in the range of 0.5 to 1.5,
   c. adding a reducing agent drop wise into the solution as obtained in step (b) with constant stirring to obtain a gel wherein the molar ratio of Cu to reducing agent is in the range of between 0.5 to 1.5,
   d. heating the gel as obtained in step (c) at temperature ranging between 30-55° C. for a period ranging between 2-4 hrs followed by heating the gel at temperature ranging between 100-200° C. hydrothermally for a period ranging between 12-30 hours to obtain solid catalyst followed by washing the solid catalyst with excess water,
   e. drying the solid catalyst as obtained in step (d) at 80-110° C. for a period in the range of 6-12 h,
   f. calcining the solid catalyst as obtained in step (e) at temperature ranging between 300-900° C. for a period of 5-12 hrs to obtain Cu—Cr oxide catalyst.

2. The process according to claim 1, wherein the surfactant used in step (b) is cetyltrimethyl ammonium bromide (CTAB).

3. The process according to claim 1, wherein the reducing agent used in step (c) is hydrazine.

4. A process for single step selective oxidation of aromatic compounds using catalyst of claim 1, wherein the process comprises the steps of:
   i) reacting aromatic substrate with an oxidant in an solvent in presence of Cu—Cr oxide catalyst as obtained in claim 1, having weight ratio of substrate to catalyst in the range of 3 to 20, having molar ratio of substrate to oxidant in the range of 1:2 to 1:30 at temperature of 30-120° C.,
   ii) agitating the reaction mixture as obtained in step i) for a period of 1-30 hours, followed by cooling to room temperature to obtain the product.

5. The process according to claim 4, wherein aromatic substrate used is selected from the group consisting of benzene, toluene and ethylbenzene.

6. The process according to claim 4, the oxidant used is $H_2O_2$.

7. The process according to claim 4, wherein the obtained products is selected from the group of phenol, benzaldehyde and acetophenone.

8. The process according to claim 4, wherein the conversion of benzene to phenol is in the range of 8-100%.

9. A process as claimed in claim 4, wherein the conversion of toluene to benzaldehyde and 5-95%.

10. The process according to claim 4, wherein the conversion of ethylbenzene to acetophenone is in the range of 20-94%.

11. The process according to claim 4, wherein the selectivity of the phenol, benzaldehyde, acetophenone is in the range of 50 to 100%.

12. The process according to claim 4, wherein yield of the phenol, benzaldehyde, acetophenone is in the range of 12-91%.

* * * * *